United States Patent [19]

Jagdmann, Jr.

[11] Patent Number: 5,432,198

[45] Date of Patent: Jul. 11, 1995

[54] VICINAL-SUBSTITUTED CARBOCYCLIC COMPOUNDS AS THERAPEUTIC AGENTS

[75] Inventor: G. Erik Jagdmann, Jr., Apex, N.C.

[73] Assignee: Sphinx Pharmaceuticals Corporation, Durham, N.C.

[21] Appl. No.: 292,753

[22] Filed: Aug. 18, 1994

[51] Int. Cl.$^6$ ............................................. A01N 37/10
[52] U.S. Cl. .................................... 514/544; 560/52; 562/460; 564/171
[58] Field of Search ........................ 560/52; 562/460; 564/171; 514/544

[56] References Cited

U.S. PATENT DOCUMENTS

| | | | |
|---|---|---|---|
| 4,153,724 | 5/1979 | Hamazaki | 560/52 |
| 4,244,880 | 1/1981 | Alexander | 560/52 |
| 5,171,882 | 12/1992 | Gapinski | 560/52 |

Primary Examiner—Paul J. Killos
Attorney, Agent, or Firm—Nath, Amberly & Associates; Gary M. Nath; Suet Chong

[57] ABSTRACT

Compounds having the formula

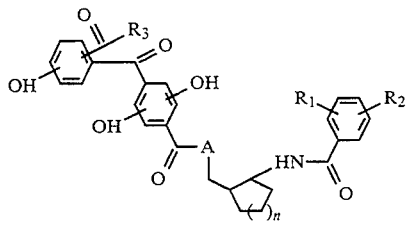

are useful as inhibitors of protein kinase C. Also disclosed are pharmaceutical compositions including such compounds and methods for using such compounds to inhibit protein kinase C in animals, including man.

13 Claims, No Drawings

VICINAL-SUBSTITUTED CARBOCYCLIC COMPOUNDS AS THERAPEUTIC AGENTS

FIELD OF THE INVENTION

The present invention relates to treatments for inflammatory, cardiovascular, metabolic, nervous system, viral infectious, neoplastic, and other diseases. The present invention provides compounds which can inhibit protein kinase C isozymes (PKC). The present invention also provides compounds useful for treating inflammatory, cardiovascular, metabolic, nervous system, viral infectious, fungal infectious, neoplastic, and other diseases; compositions and methods useful in treating such diseases; and methods for preparing such compounds.

BACKGROUND OF THE INVENTION

Inhibition of PKC presently is believed to be one of the biochemical mechanisms by which the invented compounds produce their therapeutic effects. PKC is a family of calcium- and phospholipid-dependent serine-/threonine-specific protein kinases which play an important role in cellular growth control, regulation, and differentiation. Activation of PKC has been implicated in several human disease processes including neoplasms. For example, cells transformed with the oncogenes ras, sis, erbB, abl, and src have been shown to contain elevated levels of diacylglycerol (DAG) which is believed to activate PKC. Additionally, several studies have shown increased expression of PKC in certain tumor types such as breast and lung carcinomas and activated PKC has been detected in human colon carcinomas. Further, PKC inhibitors have been reported to potentiate the antitumor activity of various chemotherapeutic agents including cis-platinum and doxorubicin.

Other human diseases in which PKC activation has been implicated include inflammatory diseases and reperfusion injury. PKC inhibitors have been demonstrated to block platelet aggregation and release of neutrophil activating agents such as platelet activating factor. PKC inhibitors also have been shown to inhibit neutrophil activation and chemotactic migration as well as neutrophil degranulation and release of proteolytic enzymes and reactive oxygen intermediates. Thus PKC inhibitors have the potential to block the most significant mechanisms of pathogenesis associated with inflammation and reperfusion injury.

PKC inhibitors which also are useful as therapeutic agents are disclosed in U.S. Ser. No. 08/025,846; 08/237,645; and 08/236,488.

SUMMARY OF THE INVENTION

The present invention resides in the discovery that compounds of Formula I, below, are useful in treating inflammatory, cardiovascular, metabolic, nervous system, viral infectious, fungal infectious, neoplastic, and other diseases. Formula I compounds inhibit PKC and inhibition of PKC is believed to be a biochemical mechanism of action of these compounds.

Presently preferred compounds of the invention include:
syn-2-[4-(2-Carboxy-6-hydroxybenzoyl)-3,5-dihydroxybenzoyloxymethyl]-1-(4-hydroxybenzamido)cyclopentane anti-2-[4-(2-Carboxy-6-hydroxybenzoyl)-3,5-dihydroxybenzoyloxymethyl]-1-(4-hydroxybenzamido)cyclopentane; and
anti-2-[4-(2-Carboxy-6-hydroxybenzoyl)-3,5-dihydroxybenzamidomethyl]-1-(4-hydroxybenzamido)cyclopentane.

The invention also includes a method for inhibiting PKC activity in mammals, including humans, which comprises administering to a subject an effective amount of one or more of the presently invented Formula I compounds. Included in the present invention are pharmaceutical compositions comprising compounds useful in the invented method and a pharmaceutical carrier.

Also included in the present invention are intermediates useful in preparing the invented Formula I compounds.

DETAILED DESCRIPTION OF THE INVENTION

The presently invented compounds that are pharmaceutically useful have the following formula:

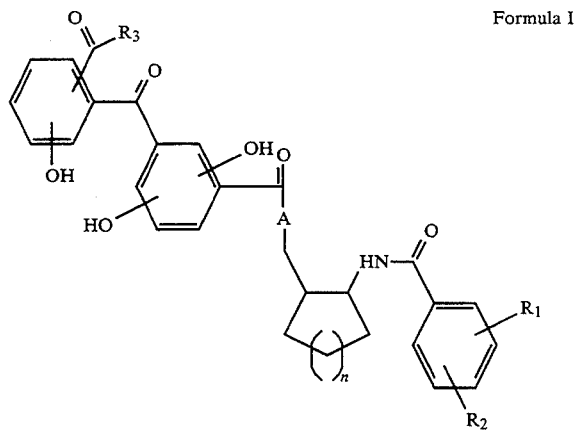

Formula I wherein:
A is O or NR4;
R4 is H or lower alkyl;
R1 and R2 are any accessible combination of hydroxy, $C_{1-6}$alkoxy, $C_{1-6}$alkoxycarbonyl, $C_{1-6}$carboxy, $C_{1-6}$acyloxy, $C_{1-6}$carboxamide, formyl, $C_{1-6}$alkyl, halo, $CF_3$, amino, $C_{1-6}$alkylamino, arylamino, $C_{1-6}$alkylsulfonyl, $C_{1-6}$alkylthio, $C_{1-6}$alkylsulfinyl;
R3 is OH, O-$C_{1-6}$alkyl, NHR5;
n is 1-3;
R5 is hydrogen, alkyl, aryl, or cycloalkyl; and
pharmaceutically acceptable salts thereof.

As used in Formula I and elsewhere in this specification and claims "$C_{x-y}$alkyl" and variations thereof are a straight chain or branched, saturated or unsaturated alkyl group containing x to y carbon atoms wherein x and y are integers and "halo" includes bromo, chloro, fluoro, and iodo. Some of the compounds included in Formula I can exist in more than one chiral form and thus exhibit stereoisomers. Formula I includes all purified stereoisomers and racemic mixtures of the compounds within its scope.

The compounds of Formula I wherein A is oxygen are prepared from corresponding cyclic ketones by known processes such as shown in Scheme I, below. The starting cyclic ketones are known and described in published references or can be obtained readily. The benzophenone compound(s) is prepared as described in Examples 1 or 2.

benzoyl chloride yields substituted benzylamide alcohols (4). Treatment of compounds (4) with substituted

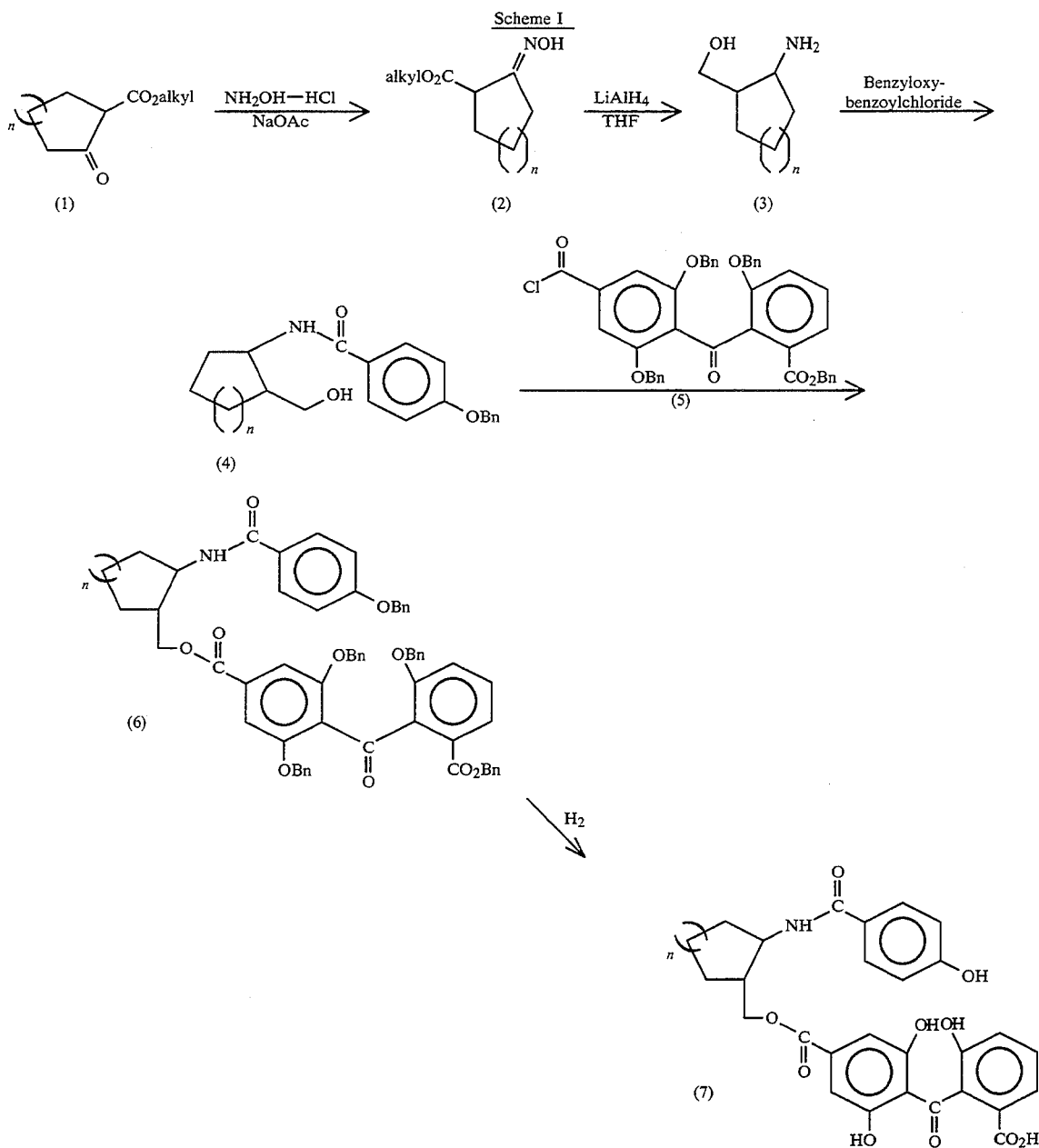

According to Scheme I, the starting ketones (1) are converted to the corresponding oximes (2) by treatment with, for example, hydroxylamine and sodium acetate. The corresponding amino alcohols (3) are prepared by reduction of oximes (2) with lithium aluminum hydride. Treatment of the amino alcohols (3) with benzyloxy-benzoylbenzoic acid chlorides (5) in methylene chloride yields formula (6) compounds which are reduced to produce formula (7) compounds which are compounds of Formula I.

Formula I compounds wherein A is NR4 are prepared by modifying Scheme I as follows:

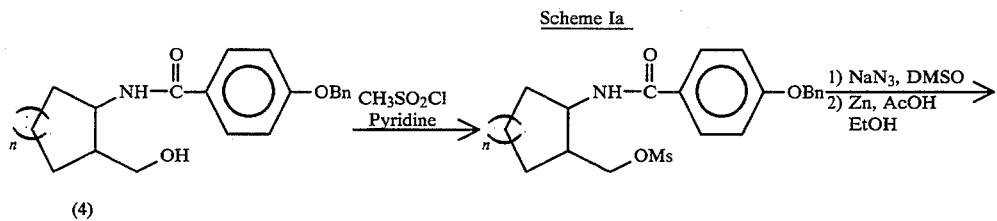

-continued
Scheme Ia

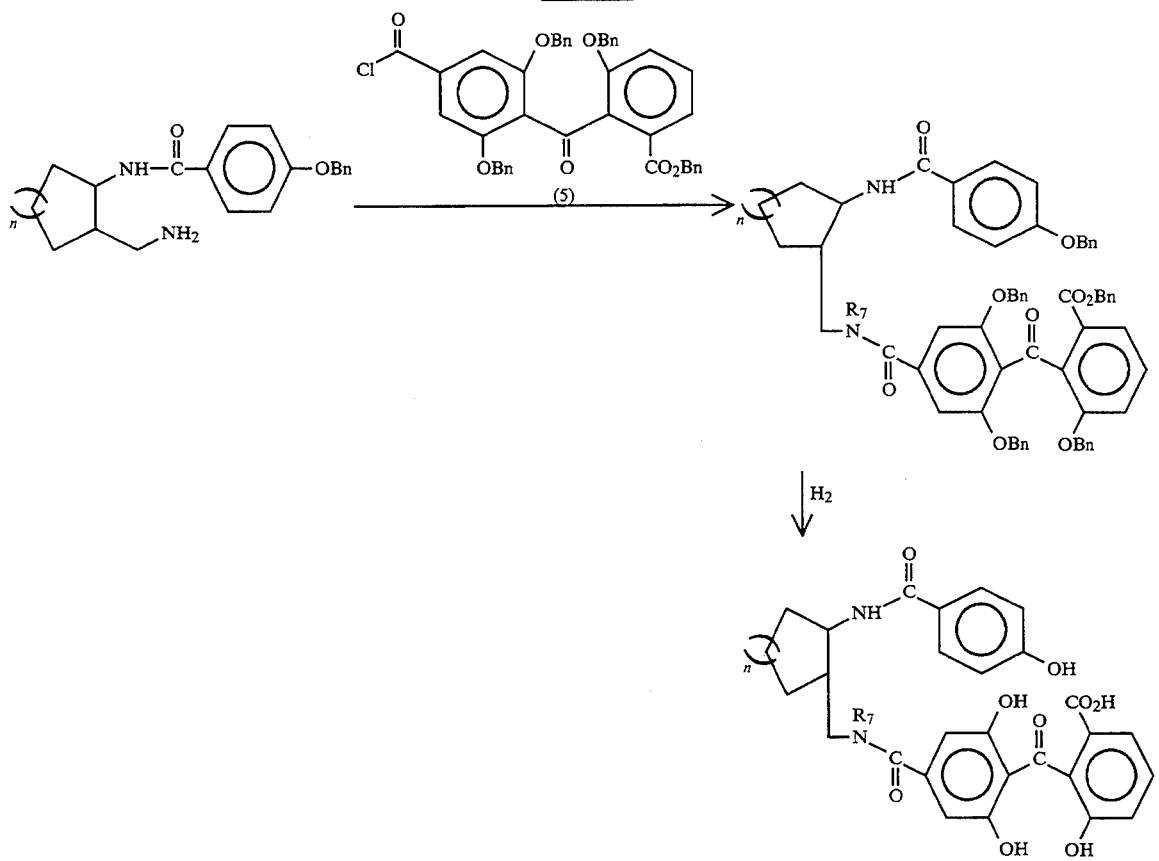

Pharmaceutically useful salts included in Formula I comprise, for example, sodium, potassium, trialkyl ammonium, calcium, zinc, lithium, magnesium, aluminum, diethanolamine, ethylenediamine, megulmine, acetate, maleate, fumarate, lactate, oxalate, methansulfonate, ethansulfonate, benzenesulfonate, tartrate, citrate, hydrochloride, hydrobromide, sulfate, phosphate, and nitrate.

The invention also includes compounds of the following Formula II which are useful in preparing the Formula I compounds:

Formula II

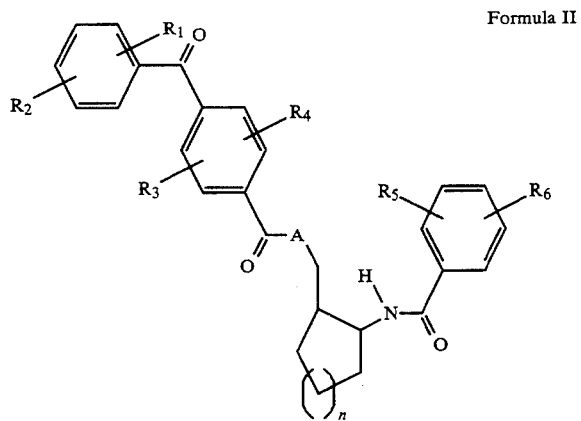

wherein:
A is O or $NR_7$;
$R_7$ is H or lower alkyl;

$R_1$, $R_2$, $R_3$, $R_4$, $R_5$, and $R_6$ are any accessible combination of OBn, $CO_2Bn$, $OCH_2Oalkyl$, or $CO_2alkyl$; and n is 1-3.

According to the invented methods Formula I compounds are used to treat diseases involving cellular growth, regulation, and differentiation such as inflammatory, cardiovascular, and neoplastic diseases. As used herein inflammatory diseases include reperfusion injuries and psoriasis and other inflammatory skin diseases. Compounds of Formula I also are used to treating fungal and viral infections. Additionally, Formula I compounds are useful in treating various central nervous system disorders such as injuries induced by ischemia and Alzheimer's disease.

At least some of the compounds included in Formula I are PKC inhibitors and presently it is believed that PKC inhibition is important in producing the therapeutic effect produced by the Formula I compounds. Compounds that inhibit PKC are identified by an assay in which radiolabelled ATP is combined with a phosphorylation acceptor molecule in the presence of PKC and a compound being tested for potency in inhibiting PKC. Various levels of test compound are used to determine the level of inhibitory activity that a particular test compound possesses. As a control, radiolabelled ATP, phosphorylation acceptor molecule, and PKC are combined without test compound. Assay conditions such as pH, salt, and cofactor conditions preferably are maintained to be similar to physiological levels. Widely used methods for determining PKC inhibition have been described by A. C. McArdle and P. M. Conn, Methods in Enzymology (1989) 168, 287; and U. Kikkawa et al., Biochem. Biophys. Res. Commun. (1986) 135, 636 and are incorporated fully herein by reference.

The Formula I compounds that have been tested for PKC inhibitory activity have been found to have IC$_{50}$'s between 20 nM and 50 μM.

Formula I compounds are formulated into acceptable pharmaceutical compositions using well known pharmaceutical chemistry methods. For example, Formula I compounds are formulated into tablets, capsules, powders, elixirs, syrups, or emulsions for oral administration; sterile solutions or emulsions for parenteral administration; or ointments or creams for topical administration. In addition to the Formula I compounds the pharmaceutical compositions of the invention may include carriers such as water, oil, saline, lactose, sucrose, mannitol, starch, or magnesium stearate; coloring agents; flavoring agents; preservatives; and stabilizing agents. Certain of the pharmaceutical compositions are formulated to provide sustained release or are film coated.

Pharmaceutical compositions including Formula I compounds are administered orally, parenterally, topically, by inhalation, optically, otically, or rectally. It presently is contemplated that the daily dosage, which may be divided, will be in the range of from about 1 μg to about 100 mg per kg of body weight, preferably from about 1 μg to about 40 mg per kg of body weight, more preferably from about 10 μg to about 20 mg per kg of body weight. The optimum dosage for treatment of human diseases is readily determinable by standard clinical research techniques.

Prodrugs are compounds that upon administration are converted to Formula I compounds and thus are equivalents of the compounds disclosed and claimed herein. Prodrugs such as carbonates and carboxy esters of phenolic hydroxy and amino groups are prepared by derivatization of the hydroxy and amino groups with acylating agents, such as methyl chloroformate, ethyl chloroformate, isobutyroyl chloride, methoxypropionyl chloride, methyl chlorosuccinate, ethyl chlorosuccinate, and benzoyl chloride, for example.

The following examples illustrate preparation of Formula I compounds. These examples do not limit the scope of the present invention as described above and claimed below.

EXAMPLE 1

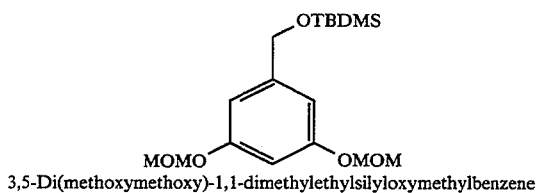

3,5-Di(methoxymethoxy)-1,1-dimethylethylsilyloxymethylbenzene

Benzophenone Reagent Preparation. MOMCl (29.8 ml, 0.393 mol) was added dropwise to a 0° C. solution of methyl 3,5-dihydroxybenzoate (30 g, 0.178 mol) and Hunig's base (57.6 g, 77.7 ml, 0.446 mol) in methylene chloride. After the final addition the reaction mixture was allowed to warm to ambient temperature and stirred overnight. This was poured into deionized water, the organics separated and washed with 10% aqueous copper sulphate solution. The organic layer was dried (MgSO$_4$), evaporated and chromatographed (SiO$_2$, 15:1 to 9:1 hexane-ethyl acetate, gradient elution). The major product was isolated as a clear colorless oil (34.5 g, 75%) and used as is in the next step.

The ester (36.0 g, 0.14 mol) was dissolved in anhydrous THF and added dropwise to a stirred solution of lithium aluminum hydride (183 ml of a 1.0M solution in THF) in dry THF. After the final addition stirring was continued for 2 h whereupon deionized water (8 ml), 15% aqueous NaOH (8 ml) and deionized water (28 ml) were sequentially added dropwise. The resulting suspension was stirred for 2 h and filtered. The solids were washed with ethyl acetate and the filtrates evaporated to provide the alcohol as a clear colorless oil (34 g) which was used in the next step without further purification.

A solution of TBDMSCl (23.3 g, 0.154 mol) in methylene chloride was added to a stirred mixture of imidazole (10.5 g, 0.154 mol) and the above prepared alcohol (32.06 g, 0.140 mol) in methylene chloride. The reaction mixture was allowed to stir at ambient temperature overnight and poured into deionized water. The organics were separated, washed with 10% aqueous copper sulphate solution, brine and dried (MgSO$_4$) and evaporated. The residue was chromatographed (SiO$_2$, 10:1 hexane-ethyl acetate) to provide the title compound as a clear colorless oil (38.9 g, 81%).

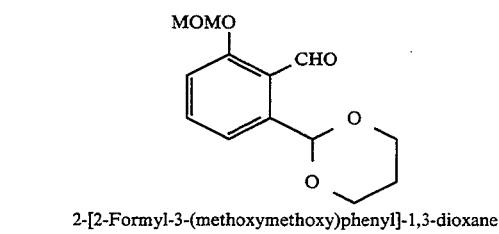

2-[2-Formyl-3-(methoxymethoxy)phenyl]-1,3-dioxane

N-BuLi (10.9 ml of a 1.6M solution in hexanes, 17.5 mmol) was added dropwise to a stirred solution of 2-[3-(methoxymethoxy)phenyl]-1,3-dioxane (3.65 g, 15.9 mmol) in anhydrous cyclohexane at ambient temperature. The mixture (which gummed up) was stirred for 15 min whereupon dry DMF (3.69 ml, 47.6 mmol) was added dropwise and stirred for an additional 15 min, quenched upon addition of brine and diluted with ethyl acetate. The organics were separated and washed with brine and deionized water, dried (MgSO$_4$) and evaporated to a light yellow gum. The aldehyde (4.0 g, 100%) was used without further purification.

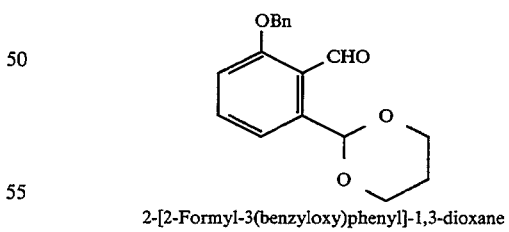

2-[2-Formyl-3(benzyloxy)phenyl]-1,3-dioxane

N-BuLi (3.98 ml of a 1.6M solution in hexanes, 6.36 mmol) was added dropwise over 10–15min to a solution of 2-[2-bromo-3-(benzyloxy)phenyl]-1,3-dioxane (2.02 g, 5.78 mmol) in dry THF at −78° C. After the final addition the mixture was stirred for an additional 30 min whereupon anhydrous DMF (4.48 ml, 57.8 mmol; 10 equivalent) was added dropwise over a period of 10 min. The resulting solution was stirred at −78° C. for 4 hr and allowed to slowly warm to ambient temperature and allowed to stir overnight (16 h). The reaction was quenched upon addition of saturated ammonium chloride extracted with ethyl acetate. The combined organics were sequentially washed with brine and water several times, dried (MgSO4) and evaporated to afford a gum which was chromatographed (SiO2, 1:1 to 2:1 methylene chloridehexanes, gradient elution) and the major component (title compound) isolated as an oil, which crystallised upon standing: mp 85°–7° C.

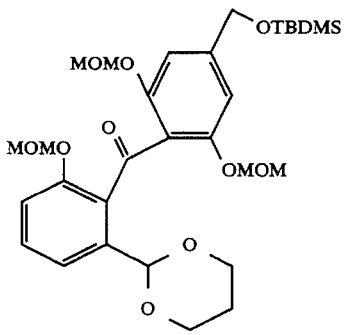

2'-(1,6-Dioxanyl)-6'-methoxymethoxy-2,6-di(methoxymethoxy)-
4-(1,1-dimethylethylsilyloxymethyl)benzophenone N-BuLi (6.80 ml of a 1.6M solution in hexanes, 10.9 mmol) was added dropwise to a solution of 3,5-di(methoxymethoxy)-1,1-dimethylethylsilyloxymethylbenzene (3.4 g, 9.93 mmol) in dry THF at 0° C. over a 5 min period. Stirring was then continued for 15 min whereupon this solution was added via cannula to a solution of the above prepared 2-[2-formyl-3-(methoxymethoxy)-phenyl]-1,3-dioxane (2.63 g, 10.4 mmol) in anhydrous THF at 0° C. The light yellow solution was then allowed to warm to ambient temperature and stirred overnight. This was quenched with brine and diluted with ethyl acetate. The layers were separated and the aqueous extracted with ethyl acetate. The combined organics were washed with brine, dried (MgSO4) and evaporated. The residue was chromatographed (2:1 hexanes-ethyl acetate) to afford the major product alcohol as a gum (2.5 g, 41%). Some impure aldehyde (500 mg) was also recovered.

N-Methyl morpholine oxide (0.80 g, 6.81 mmol) was added to a mixture of the above prepared alcohol (2.7 g, 4.54 mmol) and crushed 4A molecular sieves (which had been placed in a 110° C. oven for several hours) in dry methylene chloride. After 30 min TPAP (160 mg, 0.454 mmol) was added and the resulting solution stirred at ambient temperature for 2 days. Silica was added and the solvent removed in vacuo and placed on a dry packed column of silica and eluted with 3:1 hexane-ethyl acetate. The benzophenone (title compound) (2.34 g, 87%) was isolated as a clear colorless oil.

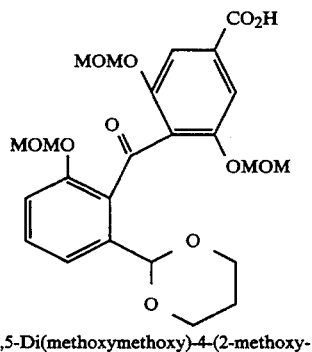

3,5-Di(methoxymethoxy)-4-(2-methoxy--continued
methoxy)-6-(1,6-dioxanyl)benzoic acid Tetrabutylammonium fluoride (45.0 ml of a 1.0M solution in THF, 44.9 mmol) was added dropwise to a stirred solution of 2'-(1,6-dioxanyl)- 6'-methoxymethoxy-2,6-di(methoxymethoxy)-4-(1,1-dimethylethylsilyloxymethyl)benzophenone, prepared as above (22.2 g, 37.4 mmol) in anhydrous THF (150 ml). After stirring for 1 h the reaction was quenched with brine and diluted with ethyl acetate. The organics were separated and the aqueous layer extracted with ethyl acetate. The combined aqueous layers were also extracted with methylene chloride. The combined ethyl acetate extracts were backwashed with brine and added to the methylene chloride layer. These combined organics were dried (MgSO4) and evaporated and the residue chromatographed (SiO, 2:1 ethyl acetate-hexanes) to provide the alcohol as an oil (13.0 g, 72%) which crystallised upon standing and was used in the next step without further purification.

Manganese dioxide (12 g) was added in portions to a stirred solution of the alcohol (14.1 g, 29.5 mmol) in methylene chloride. The mixture was stirred at ambient temperature for 2 days and the catalyst removed by filtration through Celite ®. The catalyst was washed with further methylene chloride and the filtrates evaporated to afford the aldehyde as a white foam (12.2 g, 84%).

A solution of the above prepared aldehyde (12.2 g, 24.8 mmol) and NaH2PO4 (1.04 g, 8.67 mmol; 0.35equiv.) in acetonitrile and deionized water (160 ml total volume; 6:1 v/v) was cooled in an ice-bath. Hydrogen peroxide (3 ml of a 30% solution on water) was added followed by solid sodium chlorite (4.4 g of 80%). This mixture was stirred for 1 h and the solvent was removed in vacuo. Deionized water was added and the precipitated solid collected by filtration. This was dried in vacuo to give the acid (9.11 g). The filtrates were extracted with methylene chloride, dried (MgSO4), evaporated and crystallised from ethyl acetate-hexanes to provide acid (0.8 g). These solid materials were combined to give a total yield of 9.91 g (79%) of target acid (title compound): mp 152°–3° C.

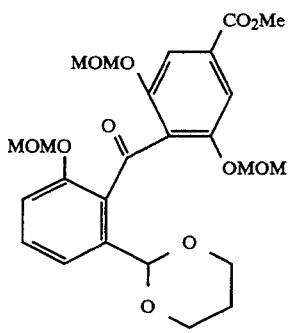

Methyl[3,5-Dimethoxymethoxy-4-(2-methoxymethoxy)-6-(1,6-dioxanyl)benzoyl]benzoate TBAF (7.96 ml of a 1.0M solution in THF, 7.96 mmol) was added dropwise to a stirred solution of 2-(1,6-dioxanyl)-6'-methoxymethoxy-2,6-di(methoxymethoxy)-4-(1,1-dimethylethylsilyloxymethyl)benzophenone, prepared as above (2.36 g, 3.98 mmol) in anhydrous THF at ambient temperature. After 1 hr brine was added and diluted with ethyl acetate. The combined organics were separated and the aqueous layer extracted with more ethyl acetate. The combined organics were washed with brine, dried (MgSO4) and evaporated to a gum (1.43 g, 75%). This material was used in the next step without further purification.

TEMPO (2.3 mg, 0.0148 mmol) was added to a solution of sodium bromide (46 mg, 0.445 mmol) and the above prepared alcohol (1.42 g, 2.97 mmol) in methylene chloride. The reaction mixture was placed in an ice bath and a freshly prepared solution of sodium bicarbonate (37 mg, 0.445 mmol) in Chlorox (4 ml) was added dropwise. Stirring was continued for an additional 30 min whereupon the reaction was quenched with solid sodium sulfite. Deionized water was added to dissolve any suspended solids and the organic layer separated, dried (MgSO4) and evaporated to afford the aldehyde (1.5 g) as a gum. This material was used in the next step without further purification.

A 0° C. solution of potassium hydroxide (0.41 g, 7.23 mmol) in methanol was added dropwise to a solution (0° C.) of the above prepared aldehyde (1.37 g, 2.78 mmol) in methanol. This was followed by the dropwise addition of a solution of iodine (0.92 g, 3.62 mmol) in methanol precooled to 0° C. After the final addition, the reaction mixture was warmed to ambient temperature and allowed to stir for 1 h, neutralised with 1N potassium hydrogen sulfate and the solvents were removed in vacuo. The residue was partitioned between ethyl acetate and brine. The organics were separated and washed with aqueous sodium thiosulfate, dried (MgSO4) and evaporated. The residue was chromatographed (SiO2, 8:5 hexane-ethyl acetate) and the ester (title compound) was isolated (819 mg) as a white foam. Alternatively this material could be concentrated and allowed to crystallise upon standing: mp 104°-5° C.

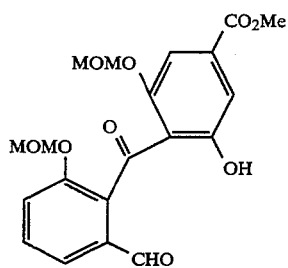

Methyl 4-[6-Formyl-2-methoxymethoxybenzoyl]-
5-hydroxy-3-methoxymethoxybenzoate

A solution of the ester prepared in the previous step (1.65 g, 3.26 mmol) in methylene chloride was added to a stirred mixture of 18% sulphuric acid adsorbed on silica (ca. 12 g). The reaction mixture was stirred at ambient temperature for 10h whereupon solid sodium carbonate was added, stirred for 5 min and filtered through a sintered funnel. The solid material was washed with methylene chloride and the filtrates were evaporated. The residue was crystallised from diethyl ether to afford aldehyde ester (title compound) (1.12 g, 63%) as a light yellow solid: mp 106°-8° C.

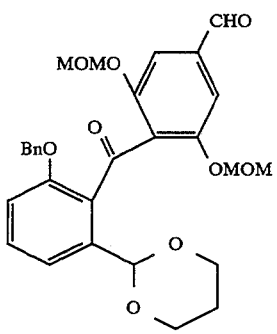

4-[(2-Benzyloxy)-6-(1,6-dioxanyl)benzoly]-
3,5-bismethoxymethoxy)benzaldehyde

N-BuLi (18.5 ml of a 2.5M solution in hexanes, 40.2 mmol) was added dropwise to a solution of MOM diether (15.8 g, 46.3 mmol) in dry THF at 0° C. over a 5 min period. Stirring was then continued for 60 min whereupon this solution was added via cannula to a solution of 2-[2-formyl-3-(benzyloxy)phenyl]-1,3-dioxane, prepared as above (12.0 g, 40.2 mmol) in anhydrous THF at 0° C. The light yellow solution was allowed to stir at 0° C. for 2 h and then allowed to warm to ambient temperature and stirring continued overnight. The reaction mixture was quenched with saturated ammonium chloride solution and diluted with ethyl acetate. The layers were separated and the aqueous layer extracted with ethyl acetate. The combined organics were washed with brine, dried (MgSO4) and evaporated. The residue was chromatographed (2:1 hexanes-ethyl acetate) to afford the alcohol as a foam (18.8 g, 73%).

The alcohol above (18.7 g, 29.2 mmol) was dissolved in methylene chloride and MnO2 (25.4 g, 0.292 mol) added in portions. The reaction mixture was allowed to stir overnight at ambient temperature at which time an additional 10 g of MnO2 was added and stirring continued for 2 days. The catalyst was removed by filtration through Celite ® and washed with more methylene chloride. The filtrates were evaporated to give the benzophenone (17.4 g, 93%) as a white foam.

TBAF (34.7 ml of a 1M solution in THF, 34.8 mmol) was added to a stirred solution of the above prepared benzophenone (18.5 g, 29.0 mmol) in anhydrous THF. After 1.5 h, brine was added and extracted twice with ethyl acetate. The aqueous layer was further extracted with methylene chloride and the ethyl acetate mixture backwashed with brine. The organics were all combined, dried (MgSO4) and evaporated. The residue was chromatographed (SiO2, 2:1 ethyl acetate-hexanes) to afford the alcohol (13.4 g, 88%) as a white solid: mp 130°-2° C.

MnO2 (ca. 10 g) was added in portions to a stirred solution of the above alcohol (13.1 g) in methylene chloride and allowed to stir for 2 days at ambient temperature. The catalyst was removed by filtration through Celite ® and the filtrates were evaporated to yield the aldehyde (title compound) (12.7 g, 97%) as a white solid: sample could be prepared by crystallisation from ethyl acetate: mp 134°-6° C.

EXAMPLE 2

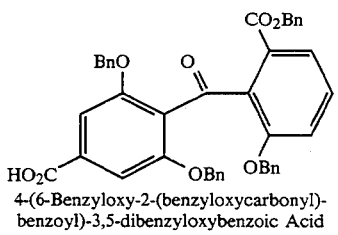

4-(6-Benzyloxy-2-(benzyloxycarbonyl)-
benzoyl)-3,5-dibenzyloxybenzoic Acid 2-(2-Bromo-3-benzyloxyphenyl)-1,3-dioxane. (2-bromo-3-benzyloxybenzyl alcohol (251 g, 0.86 mol) was dissolved in THF (300 ml) and sodium bromide (13.2 g, 0.128 mol) added. The reaction mixture was cooled to 0° C. and TEMPO (0.67 g, 4.28 mmol) was added followed by a freshly prepared (0° C.) solution of sodium bicarbonate (10.8 g, 0.128 mol) in 1 liter of commercial Chlorox ® bleach. This was stirred rapidly at 0° C. for 3 h and sodium sulfite added. Any precipitated solids were dissolved upon addition of deionized water. The organics were separated and the aqueous layer extracted with ethyl acetate. The combined organics were washed with brine, dried (MgSO$_4$) and concentrated. The residue was cooled in an ice bath and the precipitated solids collected by filtration to give 2-bromo-3-benzyloxybenzaldehyde (224 g, 90%): mp 125°-6° C. The above prepared aldehyde (215 g) was combined in toluene (200 ml) with 1,3-propane diol (107 ml, 1.48 mol) and pTSA.H$_2$O (1.6 g) and heated at the reflux temperature with azeotropic removal of water via a Dean-Stark trap. After 1.5 h the reaction mixture was cooled and washed with saturated sodium bicarbonate and brine. The organics were separated, dried (MgSO$_4$) and evaporated. The residue was crystallized from methanol to afford the title compound as a white solid (248 g, 96%): mp 73°-4° C.

2-(2-Formyl-3-benzyloxyphenyl)-1,3-dioxane. N-BuLi (236.2 ml of a 1.6 M solution in hexanes, 0.378 mol) was added dropwise to a solution of the product of the preceding reaction (120 g, 0.344 mol) in dry THF (600 ml) at −78° C. The temperature was maintained < −60° C. during this time and stirring was continued for an additional 15 minutes after the final addition. Anhydrous DMF (532.2 ml, 6.87 mol) was then added dropwise whilst maintaining temperature < −60° C. The resulting solution was stirred at −60° C. for 4 h and allowed to slowly warm to ambient temperature and allowed to stir overnight (16h). The reaction was quenched upon addition of saturation ammonium chloride solution and the solvents (THF, DMF) were removed in vacuo. The residue was partitioned between ethyl acetate and brine. The organics were sequentially washed with brine and water several times, dried (MgSO$_4$) and evaporated to a solid which was recrystallized from ethyl acetate-hexanes to give the title compound (80.7 g, 79%): mp 85°-7° C.

1,1-Dimethylethyl 4-[2-benzyloxy-6-(1,6-dioxanyl)-phenylhydroxymethyl]-3,5-dibenzyloxybenzoate. N-BuLi (77.86 ml of 2.5 M solution in hexanes, 0.195 mol) was added dropwise to a −70° C. solution of 1,1-dimethylethyl 4-bromo-3,5-dibenzyloxybenzoate (83.1 g, 0.177 mol) in anhydrous THF (800 ml) at a rate to maintain the internal temperature < −65° C. After the final addition the mixture was stirred for a further 10 minutes, whereupon the purple colored solution was added quickly via cannula to a −70° C. solution of the aldehyde (44.0 g, 0.147 mol) in dry THF (800 ml). The resulting yellow reaction mixture was stirred at this temperature overnight at which time solid ammonium chloride was added and was then allowed to warm to ambient temperature. Deionized (700 ml) water was then added and the organic layer was separated. The aqueous was extracted with ethyl acetate and the combined organics were washed with brine, dried (MgSO$_4$) and evaporated to afford a yellow oil which was chromatographed (SiO$_2$, 15% ethyl acetate-hexanes). The title compound was isolated as a white foam (62.23 g, 61%).

1,1,-Dimethylethyl 4-[2-benzyloxy-6-(1,6-dioxanyl)-benzoyl]-3,5-dibenzyloxybenzoate. Manganese dioxide (250 g) was added in portions to a stirred solution of the product of the preceding reaction (62.2 g, 0.090 mol) in methylene chloride (1.5L). The reaction mixture was allowed to stir overnight at ambient temperature and the MnO$_2$ was removed by filtration through Celite ®. The pad was washed with further methylene chloride and the filtrates were evaporated to afford the title compound.

1,1-Dimethylethyl 3,5-Dibenzyloxy-4-[6-benzyloxy-2-formylbenzoyl]benzoate. The ketone product from the preceding reaction (58.0 g, 0.084 mol) was dissolved in acetone (270 ml) and deionized water (30 ml). A catalytic amount of pTSA·H$_2$O was added and the mixture refluxed for 3 h. Saturated sodium bicarbonate solution was added to adjust the pH to a basic level and the acetone was removed in vacuo. The aqueous layer was extracted with ethyl acetate and the organics dried (MgSO$_4$) and evaporated. The residue was crystallized from methanol to afford the title compound (50.48 g, 95%) as a light yellow solid.

3-Benzyloxy-2-[2,6-dibenzyloxy-4-(1,1-dimethylethoxycarbonyl)benzoyl]benzoic acid. A solution of sulfamic acid (4.01 g, 0.041 mol) in deionized water (50 ml) was added to a solution of the aldehyde product of the previous reaction (20.0 g, 0.0318 mol) in acetonitrile (300 ml) at ambient temperature. After 5 minutes a solution of sodium chlorite (4.82 g, of 80%, 0.043 mol) in deionized water (50 ml) was added dropwise. Once complete the reaction mixture was stirred for 30 minutes. The solvent was removed in vacuo and the aqueous was extracted several times with ethyl acetate. The organics were combined, dried (MgSO$_4$) and evaporated to afford the title compound (20.9 g).

1,1-Dimethylethyl 4-(6-Benzyloxy-2-(benzyloxycarbonyl)benzoyl)-3,5-dibenzyloxybenzoate. To a solution of 5.98 g (9.28 mmol) of 3-benzyloxy-2-(2,6-dibenzyloxy-4-(1,1-dimethylethoxycarbonyl)benzoyl)benzoic acid in 75 mL of dry dimethylformamide was added 3.85 g (27.9 mmol) of potassium carbonate and 1.21 mL (1.74 g, 10.2 mmol) of benzyl bromide. The solution was stirred at room temperature under a nitrogen atmosphere for 13 h. The mixture was then poured onto 800 mL of water and extracted with three 400 mL portions of ether. The organic extracts were washed twice with water and then with brine, and dried over magnesium sulfate. Evaporation of the solvent afforded 6.76 g of the crude product, which was chromatographed on silica gel, eluting with 4/1 hexane-ethyl acetate to give 4.98 g (73%) of the title compound as a colorless oil.

4-(6-Benzyloxy-2-(benzyloxycarbonyl)benzoyl)-3,5-dibenzyloxybenzoic Acid. A solution of 0.428 g (0.582 mmol) of 1,1-dimethylethyl 4-(6-benzyloxy-2-(benzyloxycarbonyl)benzoyl)-3,5-dibenzyloxybenzoate in 5 mL of distilled quinoline was heated at 200° C. under an atmosphere of nitrogen for 3 h. The mixture was then cooled, poured onto 75 mL of ether and washed three times with 2N HCl and once with brine. The organic extracts were dried over magnesium sulfate and evaporated to give 0.42 g of the crude product, which was recrystallized from isopropanol to give 0.270 g (68%) of the title compound as a tan solid, mp 151°–156° C.

EXAMPLE 3

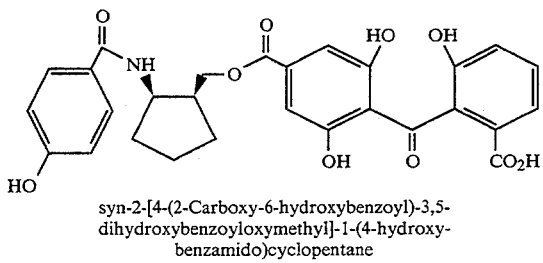

syn-2-[4-(2-Carboxy-6-hydroxybenzoyl)-3,5-dihydroxybenzoyloxymethyl]-1-(4-hydroxybenzamido)cyclopentane 2-Carbomethoxycyclopentanone, oxime A solution of 2-carbomethoxycyclopentanone (7.11 g, 50 mmol) in reagent methanol (60 mL) under nitrogen was treated with hydroxylamine hydrochloride (0.80 g, 11.5 mmol), then with sodium acetate (1.05 g, 12.8 mmol), and the mixture was stirred at 55° C. for 3h. More sodium acetate (4.1 g, 50 mmol) was added, and the mixture was cooled to room temperature, diluted with methylene chloride (150 mL), and filtered. The flitrate was concentrated in vacuo, taken up in methylene chloride, and passed through a short column of silica gel (eluted with 9:1 methylene chloride/acetone) to afford 2-carbomethoxycyclopentanone, oxime (7.80 g, 99%) as a colorless oil.

syn-1-(4-Phenylmethoxybenzamido)cyclopentan-2-methanol

A cooled (5° C.) solution of 2-carbomethoxycyclopentanone, oxime (3.93 g, 25 mmol) in anhydrous tetrahydrofuran (60 mL) under nitrogen was treated dropwise with 1.0N lithium aluminum hydride/tetrahydrofuran (100 mL, 100 mmol) at a rate to keep the pot temperature below 10° C. (slowly at first, more rapidly later). The solution was maintained at 5° C. for 3 h, allowed to slowly warm to room temperature overnight, refluxed for one hour, and cooled (−10° C.). Water (3.8 mL), 15% sodium hydroxide (3.8 mL), and water (12 mL) were carefully added at a rate to keep the pot temperature below 5° C. The mixture was stirred at room temperature for one hour, then filtered, and the filter cake was washed with tetrahydrofuran. The flitrate was concentrated in vacuo, taken up in methylene chloride (130 mL) and 1N sodium hydroxide (65 mL), and treated with 4-benzyloxybenzoyl chloride (7.4 g, 30 mmol). The solution was stirred at room temperature for 18 h and separated. The aqueous layer was extracted with methylene chloride (50 mL), and the combined organic layers were concentrated in vacuo. The residue was taken up in methanol (70 mL) and treated with potassium hydroxide (10 g) dissolved in water (30 mL). The mixture was stirred at 55° C. for 2 h, partially concentrated in vacuo to remove most of the methanol, then extracted with methylene chloride (2×50 mL). The combined extracts were dried (Na$_2$SO$_4$), concentrated in vacuo, and chromatographed on silica gel (eluted first with 10%, then 15% acetone/methylene chloride) to initially afford syn-1-(4-phenylmethoxybenzamido)cyclopentan-2-methanol (0.82 g; mp (EtOAc/hexane) 102°, 121° C. as white crystals), then anti-1-(4-phenylmethoxybenzamido)cyclopentan-2-methanol (2.85 g; mp (CH$_3$CN)143°–5° C. as fine white crystals); the combined yield was 3.67 g (45%).

syn-2-[4-(2-Benzyloxycarbonyl-6-phenylmethoxybenzoyl)-3,5-bis(phenylmethoxy)benzoyloxymethyl]-1-(4-phenylmethoxybenzamido)cyclopentane A solution of 4-(2-Benzyloxycarbonyl-6-phenylmethoxybenzoyl)-3,5-bis(phenylmethoxy)benzoic acid (0.25 g, 0.37 mmol) in anhydrous methylene chloride (2.0 mL) was treated with N,N-dimethylformamide (3 drops), then with 2.0N oxalyl chloride/methylene chloride (0.25 mL, 0.50 mmol), and was stirred for one hour under a drying tube. The solution was concentrated in vacuo, diluted with anhydrous toluene (5 mL), reconcentrated in vacuo, and placed under high vacuum for one hour. Anhydrous tetrahydrofuran (1.2 mL), N,N-dimethylformamide (0.6 mL), triethylamine (0.6 mL), and 4-dimethylaminopyridine (40 mg) were added to the flask, followed closely by syn-1-(4-phenylmethoxybenzamido)cyclopentan-2-methanol (0.10 g, 0.307 mmol). The solution was stirred at room temperature for 18 h, diluted with toluene (20 mL), washed with 0.5N sodium hydroxide (6 mL) and water (6 mL), dried (Na$_2$SO$_4$), and concentrated in vacuo. Silica gel chromatography (eluted with 5% acetone/methylene chloride) afforded syn-2-[4-( 2-benzyloxycarbonyl-6-phenylmethoxybenzoyl)-3,5-bis(phenylmethoxy)benzoyloxymethyl]-1-(4-phenylmethoxybenzamido)cyclopentane (0.285 g, 94 %) as a white foam.

syn-2-[4-(2-Carboxy-6-hydroxybenzoyl)-3,5-dihydroxybenzoyloxymethyl]-1-(4-hydroxybenzamido)cyclopentane A solution of syn-2-[4-(2-benzyloxycarbonyl-6-phenylmethoxybenzoyl)-3,5bis(phenylmethoxy)benzoyloxymethyl]-1-(4-phenylmethoxybenzamido)cyclopentane (0.28 g, 0.284 mmol) in 4:1 ethanol/ethyl acetate (25 mL) in a 500 mL Parr bottle was treated with trifluoroacetic acid (0.14 mL) and purged with nitrogen. Pearlman's catalyst (20% Pd(OH)$_2$/C, 120 mg) was added, and the vessel was charged with hydrogen (50 psi) on a Parr apparatus and shaken for 18 h. The bottle was carefully evacuated of hydrogen and the solution was filtered through Celite ®, then the filter cake was washed with ethanol but not allowed to dry. The flitrate was concentrated in vacuo to a yellow foam, which was dissolved in N,N-dimethylformamide (0.8 mL) and loaded onto HPLC; conditions: A- 0.1%TFA/5%CH3CN/H2O, B-CH3CN, 100% A to 100% B over one hour, 25 mL/min, 41×250 mm C18 column. Fractions (one/min) 34–36 were combined, partially concentrated in vacuo, treated with a little acetonitrile (product not water soluble), and freeze-dried overnight to afford syn-2-[4-(2-carboxy-6-hydroxybenzoyl)-3,5-dihydroxybenzoyloxymethyl]-1-(4-hydroxybenzamido)cyclopentane(0.131 g, 79%) as a voluminous yellow solid; mp 155°–160° C. Anal. Calcd. for C$_{28}$H$_{25}$NO$_{10}$·0.3C$_2$HF$_3$O$_2$·0.5H$_2$O: C, 59.34; H, 4.62; N, 2.86. Found: C, 59.08; H, 4.62; N, 2.79.

[This space intentionally left blank]

EXAMPLE 4

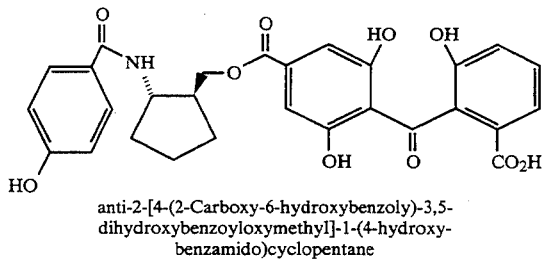

anti-2-[4-(2-Carboxy-6-hydroxybenzoly)-3,5-dihydroxybenzoyloxymethyl]-1-(4-hydroxybenzamido)cyclopentane anti-1-(4-Phenylmethoxybenzamido)cyclopentan-2-methanol A cooled (5° C.) solution of 2-carbomethoxycyclopentanone, oxime (3.93 g, 25 mmol) in anhydrous tetrahydrofuran (60 mL) under nitrogen was treated dropwise with 1.0N lithium aluminum hydride/ tetrahydrofuran (100 mL, 100 mmol) at a rate to keep the pot temperature below 10° C. (slowly at first, more rapidly later). The solution was maintained at 5° C. for 3 h, allowed to slowly warm to room temperature overnight, refluxed for one hour, and cooled (−10° C.). Water (3.8 mL), 15% sodium hydroxide (3.8 mL), and water (12 mL) were carefully added at a rate to keep the pot temperature below 5° C. The mixture was stirred at room temperature for one hour, then filtered, and the filter cake was washed with tetrahydrofuran. The flitrate was concentrated in vacuo, taken up in methylene chloride (130 mL) and 1N sodium hydroxide (65 mL), and treated with 4-benzyloxybenzoyl chloride (7.4 g, 30 mmol). The solution was stirred at room temperature for 18 h and separated. The aqueous layer was extracted with methylene chloride (50 mL), and the combined organic layers were concentrated in vacuo. The residue was taken up in methanol (70 mL) and treated with potassium hydroxide (10 g) dissolved in water (30 mL). The mixture was stirred at 55° C. for 2 h, partially concentrated in vacuo to remove most of the methanol, then extracted with methylene chloride (2×50 mL). The combined extracts were dried (Na2SO4), concentrated in vacuo, and chromatographed on silica gel (eluted first with 10%, then 15% acetone/methylene chloride) to initially afford syn-1-( 4-phenylmethoxybenzamido)cyclopentan-2-methanol (0.82 g; mp (EtOAc/hexane) 102°, 121° C. as white crystals), then anti-1-(4-phenylmethoxybenzamido)cyclopentan-2-methanol (2.85 g; mp (CH3CN) 143°-5° C. as fine white crystals); the combined yield was 3.67 g (45%).

anti-2-[4-(2-Benzyloxycarbonyl-6-phenylmethoxybenzoyl)-3,5-bis(phenylmethoxy)benzoyloxymethyl]-1-(4-phenylmethoxybenzamido)cyclopentane A solution of 4-(2-benzyloxycarbonyl-6-phenylmethoxybenzoyl)-3,5-bis(phenylmethoxy)benzoic acid (0.25 g, 0.37 mmol) in anhydrous methylene chloride (2.0 mL) was treated with N,N-dimethylformamide (3 drops), then with 2.0N oxalyl chloride/methylene chloride (0.25 mL, 0.50 mmol), and was stirred for one hour under a drying tube. The solution was concentrated in vacuo, diluted with anhydrous toluene (5 mL), reconcentrated in vacuo, and placed under high vacuum for one hour. Anhydrous tetrahydrofuran (1.2 mL), N,N-dimethylformamide (0.6 mL), triethylamine (0.6 mL), and 4-dimethylaminopyridine (40 mg) were added to the flask, followed closely by anti-1-(4-phenylmethoxybenzamido)cyclopentan-2-methanol (0.10 g, 0.307 mmol). The solution was stirred at room temperature for 18 h, diluted with toluene (20 mL), washed with 0.5N sodium hydroxide (6 mL) and water (6 mL), dried (Na2SO4), and concentrated in vacuo. Silica gel chromatography (eluted with 5% acetone/methylene chloride) afforded anti-2-[4-(2-benzyloxycarbonyl-6-phenylmethoxybenzoyl)-3,5-bis(phenylmethoxy)benzoyloxymethyl]-1-(4-phenylmethoxybenzamido)cyclopentane (0.292 g, 96%) as a white foam.

anti-2-[4-(2-Carboxy-6-hydroxybenzoyl)-3,5-dihydroxybenzoyloxymethyl]-1-(4-hydroxybenzamido)cyclopentane A solution of anti-2-[4-(2-benzyloxycarbonyl-6-phenylmethoxybenzoyl)-3,5bis(phenylmethoxy)benzoyloxymethyl]-1-(4-phenylmethoxybenzamido)cyclopentane (0.29 g, 0.294 mmol) in 4:1 ethanol/ethyl acetate (25 mL) in a 500 mL Parr bottle was treated with trifluoroacetic acid (0.14 mL) and purged with nitrogen. Pearlman's catalyst (20% Pd(OH)2/C, 120 mg) was added, and the vessel was charged with hydrogen (50 psi) on a Parr apparatus and shaken for 18 h. The bottle was carefully evacuated of hydrogen and the solution was filtered through Celite ®, then the filter cake was washed with ethanol but not allowed to dry. The flitrate was concentrated in vacuo to a yellow foam, which was dissolved in N,N-dimethylformamide (0.8 mL) and loaded onto HPLC; conditions: A-0.1%TFA/5%CH3CN/H2O, B-CH3CN, 100% A to 100% B over one hour, 25 mL/min, 41×250 mm C18 column. Fractions (one/min) 36–38 were combined, partially concentrated in vacuo, treated with a little acetonitrile (product not water soluble), and freeze-dried overnight to afford anti-2-[4-(2-carboxy-6-hydroxybenzoyl)-3,5-dihydroxybenzoyloxymethyl]-1-(4-hydroxybenz-amido)cyclopentane (0.155 g, 90%) as a voluminous yellow solid; mp 167°–174° C. Anal. Calcd. for $C_{28}H_{25}NO_{10} \cdot 0.3C_2HF_3O_2 \cdot H_2O$: C, 58.45; H, 4.68;N, 2.38. Found: C, 58.08; H, 4.49; N, 2.51.

EXAMPLE 5

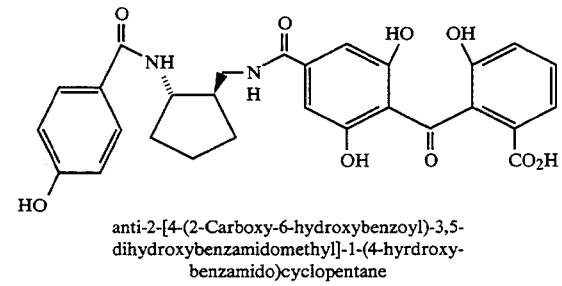

anti-2-[4-(2-Carboxy-6-hydroxybenzoyl)-3,5-dihydroxybenzamidomethyl]-1-(4-hyrdroxybenzamido)cyclopentane anti-1-(4-Phenylmethoxybenzamido)cyclopentan-2-methanamine A cooled (5° C.) solution of anti-1-(4-phenylmethoxybenzamido)cyclopentan-2-methanol (0.325 g, 1.0 mmol) in anhydrous pyridine (1.5 mL) under nitrogen was treated dropwise with methanesulfonyl chloride (0.090 mL, 1.16 mmol), and the solution was stirred at 5° C. for one hour. Sodium azide (0.52 g, 8.0 mmol) and anhydrous dimethylsulfoxide (2.0 mL) were added, and the solution was partially concentrated in vacuo at 50° C. to remove pyridine, then stirred at 60° C. for 1.5 h. The suspension was added to water (20 mL), and the cloudy solution was extracted with ether (3×30 mL). The combined organic solution was dried (MgSO4) and concentrated in vacuo to a white solid (0.32 g). This was taken up in 6:1:1 ethanol/acetic acid/water (12 mL) and treated with zinc (0.52 g, 8.0 mmol), then stirred at room temperature for 45 min and at 55° C. for 45 min. The solution was filtered and the flitrate was concentrated in vacuo and taken up in 0.5N sodium hydroxide (15 mL). Methylene chloride (40 mL) was added, and the mixture was shaken and filtered through Celite ® (filter cake washed with methylene chloride and water). The flitrate was separated and the aqueous layer was extracted with methylene chloride (2×25 mL). The combined organic extracts were dried (Na₂SO₄) and concentrated in vacuo to afford anti-1-(4-phenylmethoxybenzamido)cyclopentan-2-methanamine (0.30 g, 92%) as a pale yellow solid, somewhat crude but useable as is.

anti-2-[4-(2-Benzyloxycarbonyl-6-phenylmethoxybenzoyl)-3,5-bis(phenylmethoxy)benzamidomethyl]-1-(4-phenylmethoxybenzamido)cyclopentane A solution of 4-(2-benzyloxycarbonyl-6-phenylmethoxybenzoyl)-3,5-bis(phenylmethoxy)benzoic acid (0.34 g, 0.50 mmol) in anhydrous methylene chloride (3.0 mL) was treated with N,N-dimethylformamide (4 drops), then with 2.0N oxalyl chloride/methylene chloride (0.40 mL, 0.80 mmol), and was stirred for one hour under a drying tube. The solution was concentrated in vacuo, diluted with anhydrous toluene (10 mL), reconcentrated in vacuo, and placed under high vacuum for one hour. Crudeanti-1-(4-Phenylmethoxybenzamido)-cyclopentan-2-methanamine (0.23 g, 0.71 mmol) was dissolved in methylene chloride (4 mL) and added to the flask containing acid chloride, followed by 1.0N sodium hydroxide (2 mL). The mixture was stirred for one hour, diluted with water (8 mL) and methylene chloride (25 mL), and the organic layer was separated. The aqueous solution was extracted with methylene chloride (20 mL) and the combined organic solution was dried (Na₂SO₄) and concentrated in vacuo. The residue was chromatographed on silica gel (eluted with 3%, then 4%, then 5% acetone/methylene chloride) to afford anti-2-[4-(2-benzyloxycarbonyl-6-phenylmethoxybenzoyl)-3,5-bis(phenylmethoxy)benzamidomethyl]-1-(4-phenylmethoxybenz-amido)cyclopentane (0.383 g, 78%) as a white foam.

anti-2-[4-(2-Carboxy-6-hydroxybenzoyl)-3,5-dihydroxybenzamidomethyl]-1-(4-hydroxybenzamido)cyclopentane A solution of anti-2-[4-(2-benzyloxycarbonyl-6-phenylmethoxybenzoyl)-3,5bis(phenylmethoxy)benzamidomethyl]-1-(4-phenylmethoxybenzamido)cyclopentane (0.38 g, 0.386 mmol) in 5:1 ethanol/ethyl acetate (30 mL) in a 500 mL Parr bottle was purged with nitrogen. Pearlman's catalyst (20% Pd(OH)₂/C, 140 mg) was added, and the vessel was charged with hydrogen (50 psi) on a Parr apparatus and shaken for 18 h. The bottle was carefully evacuated of hydrogen and the solution was filtered through Celite ®, then the filter cake was washed with ethanol but not allowed to dry. The filtrate was concentrated in vacuo to a yellow foam, which was dissolved in N,N-dimethylformamide (0.8 mL) and loaded onto HPLC; conditions: A-0.1%TFA/5%CH3CN/H2O, B-CH3CN, 100% A to 100% B over one hour, 25 mL/min, 41×250 mm C18 column. Fractions (one/min) 33–35 were combined, partially concentrated in vacuo, treated with a little acetonitrile (product not water soluble), and freeze-dried overnight to afford anti-2-[4-(2-carboxy-6-hydroxybenzoyl)-3,5-dihydroxybenzamidomethyl]-1-(4-hydroxybenzamido)cyclo (0.155 g, 90%) as a volu-minous yellow solid; mp 175°–180° C. Anal. Calcd. for $C_{28}H_{26}N_2O_9 \cdot 0.4C_2HF_3O_2 \cdot H_2O$: C, 57.83; H, 4.79; N, 4.68. Found: C, 57.60; H, 4.64; N, 4.67.

EXAMPLE 6

An oral dosage form for administering the presently invented compounds is produced by screening, mixing, and filling into a hard gelatin capsule the ingredients in Table 1 below.

TABLE 1

| Ingredients | Amounts |
|---|---|
| anti-2-[4-(2-Carboxy-6-hydroxybenzoyl)-3,5-dihydroxybenzoyloxymethyl]-1-(4-hydroxybenzamido)cyclopentane | 50 mg |
| magnesium stearate | 5 mg |
| lactose | 75 mg |

EXAMPLE 7

The sucrose, calcium sulfate dihydrate and pyridylimidazole shown in Table 2 below, are mixed and granulated with a 10% gelatin solution. The wet granules are screened, dried, mixed with the starch, talc and stearic acid, screened and compressed into a tablet.

TABLE 2

| Ingredients | Amounts |
|---|---|
| anti-2-[4-(2-Carboxy-6-hydroxybenzoyl)-3,5-dihydroxybenzamidomethyl]1-(4-hydroxybenzamido)cyclopentane | 100 mg |
| calcium sulfate dihydrate | 150 mg |
| sucrose | 20 mg |
| starch | 10 mg |
| talc | 5 mg |

EXAMPLE 8 anti-2-[4-(2-Carboxy-6-hydroxybenzoyl)-3,5-dihydroxybenzoyloxymethyl]-1-(4-hydroxybenzamido)cyclopentane, 75 mg, is dispersed in 25 ml of normal saline to prepare an injectable preparation.

While the preferred embodiments of the invention are illustrated by the above, it is to be understood that the invention is not limited to the precise instructions disclosed herein and that the exclusive right to all modifications within the scope of the following claims and all equivalents thereof is reserved.

What is claimed is:

1. A compound represented by the formula:

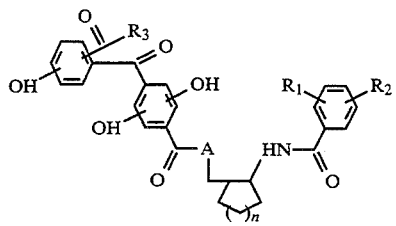

wherein:
A is O or NR₄;
R₄ is H or lower alkyl;
R₁ and R₂ are any accessible combination of hydroxy, C1-6 alkoxy, $C_{1-6}$alkoxycarbonyl, $C_{1-6}$carboxy, $C_{1-6}$acyloxy, $C_{1-6}$carboxamide, formyl, $C_{1-6}$alkyl, halo, $CF_3$, amino, $C_{1-6}$alkylamino, arylamino, $C_{1-6}$alkylsulfonyl, $C_{1-6}$alkylthio, $C_{1-6}$alkylsulfinyl;

$R_3$ is OH, O-lower alkyl, $NHR_4$ $R_5$ is hydrogen, alkyl, aryl or cycloalkyl n is 1—3; and pharmaceutically acceptable salts thereof.

2. A compound of claim 1 wherein

A is O or NH;

$R_1$ and $R_2$ are a combination of hydroxy, $C_{1-6}$carboxy, $C_{1-6}$acyloxy, $C_{1-6}$alkoxy, and $C_{1-6}$alkoxycarbonyl.

$R_3$ is OH or $OCH_3$; and n=1.

3. A compound of claim 1 that is syn-2-[4-(2-Carboxy-6-hydroxybenzoyl)-3,5-dihydroxybenzoyloxymethyl]-1-(4-hydroxybenzamido)cyclopentane anti-2-[4-(2-Carboxy-6-hydroxybenzoyl)-3,5-dihydroxybenzoyloxymethyl]-1-(4-hydroxybenzamido)cyclopentane; or anti-2-[4-(2-Carboxy-6-hydroxybenzoyl)-3,5-dihydroxybenzamidomethyl]-1-(4-hydroxybenzamido)-cyclopentane.

4. A pharmaceutical composition useful for producing a therapeutic effect that comprises a pharmaceutically acceptable carrier and a compound of claim 1.

5. A pharmaceutical composition useful for producing a therapeutic effect that comprises a pharmaceutically acceptable carrier and a compound of claim 2.

6. A pharmaceutical composition useful for producing a therapeutic effect that comprises a pharmaceutically acceptable carrier and a compound of claim 3.

7. A method for producing PKC inhibition in mammals which comprises:

administering to a subject an effective amount of a compound of claim 1.

8. A method for producing PKC inhibition in mammals which comprises:

administering to a subject an effective amount of a compound of claim 2.

9. A method for producing PKC inhibition in mammals which comprises:

administering to a subject an effective amount of a compound of claim 3.

10. A method of treating cardiovascular, metabolic, nervous system, viral infectious, fungal infectious or neoplastic diseases that comprises:

administering to a subject affected by any such diseases an effective amount of a compound of claim 1.

11. A method of treating cardiovascular, metabolic, nervous system, viral infectious, fungal infectious or neoplastic diseases that comprises:

administering to a subject affected by any such diseases an effective amount of a compound of claim 2.

12. A method of treating cardiovascular, metabolic, nervous system, viral infectious, fungal infectious or neoplastic diseases that comprises:

administering to a subject affected by any such diseases an effective amount of a compound of claim 3.

13. A compound represented by the formula

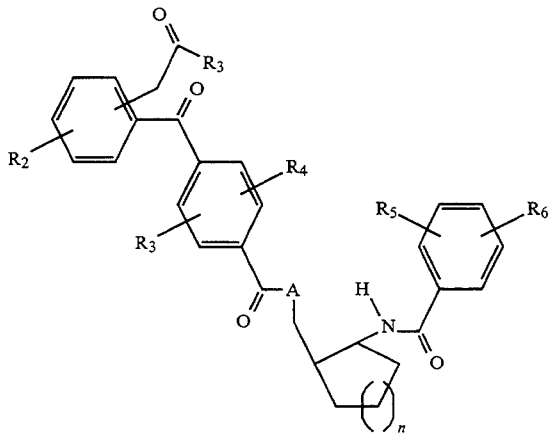

wherein:

A is O or $NR_7$;

$R_7$ is H or $C_{1-6}$ akyl;

$R_1$, $R_2$, $R_3$, $R_4$, $R_5$, and $R_6$, are any accessible combination of OBn, $CO_2Bn$, $OCH_2Oalkyl$, or $CO_2alkyl$; and n is 1-3.

* * * * *